United States Patent
Tsukamoto et al.

(10) Patent No.: US 12,365,652 B2
(45) Date of Patent: Jul. 22, 2025

(54) METHOD FOR PRODUCING ε-CAPROLACTAM

(71) Applicant: TORAY INDUSTRIES, INC., Tokyo (JP)

(72) Inventors: Daijiro Tsukamoto, Kanagawa (JP); Kenji Kawamura, Kanagawa (JP); Katsushige Yamada, Kanagawa (JP); Masato Akahira, Aichi (JP); Daisuke Yamamoto, Aichi (JP)

(73) Assignee: TORAY INDUSTRIES, INC., Tokyo (JP)

( * ) Notice: Subject to any disclaimer, the term of this patent is extended or adjusted under 35 U.S.C. 154(b) by 565 days.

(21) Appl. No.: 17/777,739

(22) PCT Filed: Nov. 18, 2020

(86) PCT No.: PCT/JP2020/042999
§ 371 (c)(1),
(2) Date: May 18, 2022

(87) PCT Pub. No.: WO2021/100759
PCT Pub. Date: May 27, 2021

(65) Prior Publication Data
US 2022/0411379 A1 Dec. 29, 2022

(30) Foreign Application Priority Data

Nov. 19, 2019 (JP) ................................. 2019-208677

(51) Int. Cl.
*C07D 223/10* (2006.01)
*C07C 227/12* (2006.01)
*C07C 229/08* (2006.01)

(52) U.S. Cl.
CPC ................. *C07D 223/10* (2013.01)

(58) Field of Classification Search
CPC .... C07D 223/10; C07C 227/12; C07C 229/08
See application file for complete search history.

(56) References Cited

U.S. PATENT DOCUMENTS

| | | | |
|---|---|---|---|
| 3,658,810 | A | 4/1972 | Tanaka et al. |
| 5,668,277 | A | 9/1997 | Hendrix et al. |
| 5,814,508 | A | 9/1998 | Di Cosimo et al. |
| 6,331,624 | B1 | 12/2001 | Koch et al. |

FOREIGN PATENT DOCUMENTS

| | | |
|---|---|---|
| CN | 1141290 A | 1/1997 |
| CN | 1450988 A | 10/2003 |
| EP | 3 553 048 A1 | 10/2019 |
| JP | 46-31539 B1 | 9/1971 |
| JP | 49-9473 B1 | 3/1974 |
| JP | 8-301843 A | 11/1996 |
| JP | 2003-530380 A | 10/2003 |
| WO | WO 01/77068 A2 | 10/2001 |

OTHER PUBLICATIONS

Japanese Office Action for Japanese Application No. 2021-504840, dated Oct. 15, 2024, with English translation.
Extended European Search Report for European Application No. 20890793.1, dated Dec. 13, 2023.
Chinese Office Action for Chinese Application No. 202080078754.2, dated Sep. 8, 2024, with English translation.
Hann et al., "5-Cyanovaleramide Production using Immobilized Pseudomonas chlororaphis B23", Bioorganic & Medicinal Chemistry, (1999), vol. 7, p. 2239-2245.
International Search Report, issued in PCT/JP2020/042999, PCT/ISA/210, dated Jan. 19, 2021.
Written Opinion of the International Searching Authority, issued in PCT/JP2020/042999, PCT/ISA/237, dated Jan. 19, 2021.
Japanese Office Action for Japanese Application No. 2021-504840, dated Jan. 28, 2025, with an English translation.

*Primary Examiner* — Brenda L Coleman
(74) *Attorney, Agent, or Firm* — Birch, Stewart, Kolasch & Birch, LLP

(57) ABSTRACT

The present invention relates to a method of producing ε-caprolactam, the method including the following steps (A) and (B): (A) a step of reacting 5-cyanovaleramide with hydrogen in an aqueous solvent in a presence of a hydrogenation catalyst to obtain a 5-cyanovaleramide hydrogenation reaction mixture; (B) a step of heating the 5-cyanovaleramide hydrogenation reaction mixture at a temperature of 180° C. or higher and 300° C. or lower in an aqueous solvent to obtain ε-caprolactam.

7 Claims, No Drawings

METHOD FOR PRODUCING ε-CAPROLACTAM

TECHNICAL FIELD

The present invention relates to a method of producing ε-caprolactam that is a raw material for a polyamide.

BACKGROUND ART

ε-Caprolactam is an important chemical raw material that is a raw material for a polyamide and is industrially produced all over the world, and most of it is used as a raw material for Nylon 6 that is a polyamide. As an industrial production method for ε-caprolactam, a production method from cyclohexanone oxime using the Beckmann rearrangement reaction with fuming sulfuric acid has been widely adopted. However, since a large amount of ammonium sulfate is produced as a by-product in the neutralization step in the Beckmann rearrangement reaction, it is required to develop a method for producing ε-caprolactam, which does not produce ammonium sulfate as a by-product. As an alternative method thereof, a method for producing ε-caprolactam from butadiene via adiponitrile synthesis from butadiene, subsequent 5-cyanovaleramide synthesis from adiponitrile, and further subsequent ε-caprolactam synthesis from 5-cyanovaleramide has been studied. (Non-Patent Literature 1).

In the ε-caprolactam synthesis from 5-cyanovaleramide, which is the final step in the above alternative method using butadiene as a raw material, a method for synthesizing ε-caprolactam by hydrogenating 5-cyanovaleramide to convert it to 6-aminocaproic acid amide and subsequently condensing 6-aminocaproic acid amide has been proposed.

For example, Patent Literature 1 discloses a method for synthesizing ε-caprolactam by reacting 5-cyanovaleramide with hydrogen in the presence of a metal catalyst to obtain 6-aminocaproic acid amide and subsequently reacting 6-aminocaproic acid amide by means of any method. It is disclosed that liquid ammonia is more preferable than an aqueous solvent as the solvent used in this method and, in the examples of this Literature, the yield of 6-aminocaproic acid amide by hydrogenation of 5-cyanovaleramide becomes low in the reaction in an aqueous solvent.

Patent Literature 2 discloses a method for producing ε-caprolactam by heating 6-aminocaproic acid amide in water at a temperature of 150° C. or higher and a critical temperature (374° C.) of water or lower. In this method, when pure 6-aminocaproic acid amide is reacted in water at 320° C., ε-caprolactam is quantitatively produced, but at 250° C., the yield of ε-caprolactam is as low as 79%.

CITATION LIST

Patent Literature

PATENT LITERATURE 1: WO2001/077068
PATENT LITERATURE 2: JP-A-S49-9473

Non-Patent Literature

NON-PATENT LITERATURE 1: Bioorganic and Medicinal Chemistry, vol. 7.2239-2245 (1999)

SUMMARY OF INVENTION

Problem to be Solved by the Invention

In the case where a chemical conversion reaction in a solvent is industrially carried out, it is desirable to use a solvent having a smaller environmental load (specifically, an aqueous solvent) from the viewpoint of green chemistry, and to carry out at a reaction temperature as low as possible (specifically, at a reaction temperature of 300° C. or lower) from the viewpoint of reducing the energy load. As mentioned above, in the case of synthesizing ε-caprolactam from 5-cyanovaleramide, a method that can synthesize ε-caprolactam in high yield while satisfying these requirements has not been found. Therefore, it is an object of the present invention to provide a method for synthesizing ε-caprolactam from 5-cyanovaleramide in high yield in an aqueous solvent at a reaction temperature of 300° C. or lower.

Means for Solving the Problem

As a result of extensive studies to solve the above problem, the present inventors have found that ε-caprolactam can be synthesized in high yield by a step of reacting 5-cyanovaleramide with hydrogen in an aqueous solvent in the presence of a hydrogenation catalyst to obtain a 5-cyanovaleramide hydrogenation reaction mixture and by heating the 5-cyanovaleramide hydrogenation reaction mixture obtained in the above step at a temperature of 180° C. or higher and 300° C. or lower in an aqueous solvent, and they have accomplished the present invention.

That is, the present invention is composed of the following (1) to (8).

(1) A method of producing ε-caprolactam, the method including the following steps (A) and (B):
  (A) a step of reacting 5-cyanovaleramide with hydrogen in an aqueous solvent in a presence of a hydrogenation catalyst to obtain a 5-cyanovaleramide hydrogenation reaction mixture;
  (B) a step of heating the 5-cyanovaleramide hydrogenation reaction mixture at a temperature of 180° C. or higher and 300° C. or lower in an aqueous solvent to obtain ε-caprolactam.

(2) The method according to (1), in which the step (A) is performed in an absence of ammonia.

(3) The method according to (1) or (2), in which a reaction temperature in the step (A) is 50° C. or higher and 200° C. or lower.

(4) The method according to any one of (1) to (3), in which the temperature of the step (B) is 200° C. or higher and lower than 280° C.

(5) The method according to any one of (1) to (4), in which the step (B) is performed in an absence of a catalyst.

(6) The method according to any one of (1) to (5), in which a ratio of 6-aminocaproic acid amide contained in the 5-cyanovaleramide hydrogenation reaction mixture is 45 mol % or more and 72 mol % or less.

(7) A 5-cyanovaleramide hydrogenation reaction mixture having a ratio of 6-aminocaproic acid amide of 45 mol % or more and 72 mol % or less.

(8) An ε-caprolactam composition having a ratio of 6-aminocaproic acid amide to ε-caprolactam of 0.1 mol % or more and 5 mol % or less.

Advantageous Effects of Invention

According to the present invention, ε-caprolactam can be produced from 5-cyanovaleramide in high yield while reducing the environmental load and the energy load.

EMBODIMENTS FOR CARRYING OUT THE INVENTION

Hereinafter, the present invention will be described in more detail, but the present invention is not limited to the following embodiments.

[Step (A)]

In the present invention, firstly as the step (A), 5-cyanovaleramide is reacted with hydrogen in an aqueous solvent in the presence of a hydrogenation catalyst to obtain a 5-cyanovaleramide hydrogenation reaction mixture.

5-Cyanovaleramide is a cyano group-containing carboxylic acid amide, which is also called 5-cyanopentanamide. 5-Cyanovaleramide can be synthesized by hydration of one cyano group of adiponitrile (e.g., Bioorganic and Medicinal Chemistry, vol. 7, 2239-2245 (1999)) or by dehydration of one amide group of adipamide (e.g., U.S. Pat. No. 3,331,866).

5-Cyanovaleramide used as a raw material in the present invention is not particularly limited, and 5-cyanovaleramide biologically and/or chemically synthesized from all kinds of carbon-containing raw materials, for example, fossil resources such as petroleum, coal and natural gas, biomass resources, and inorganic substances containing a carbon atom such as carbon monoxide, carbon dioxide and carbonate salts can be used as a raw material for ε-caprolactam.

In the present invention, the aqueous solvent means water or a water-miscible organic solvent containing water at a water ratio of more than 10% by volume. The ratio of water in the water-containing water-miscible organic solvent is preferably 30% by volume or more, more preferably 50% by volume or more, further preferably 60% by volume or more, and particularly preferably 90% or more. Specific examples of the water-miscible organic solvent that can be used in the present invention include methanol, ethanol, n-propanol, isopropanol, n-butanol, isobutanol, tert-butanol, 1,2-dimethoxyethane, diglyme, tetrahydrofuran, dioxane, γ-butyrolactone, N-methylpyrrolidone, dimethyl sulfoxide, dimethylformamide, dimethylacetamide and acetone.

The pH of the aqueous solvent is not particularly limited, but is preferably pH 2 to 13, more preferably pH 3 to 11, and further preferably pH 4 to 10, in consideration of suppression of catalyst deterioration, suppression of production of by-products, corrosiveness to the reaction apparatus, and the like.

In the present invention, the hydrogenation catalyst means a metal and/or an organometallic complex having a hydrogenation ability. Here, to have a hydrogenation ability means to have an ability to add a hydrogen atom to an unsaturated bond such as a carbon-carbon double bond (C=C), a carbon-carbon triple bond (C≡C), a carbon-oxygen double bond (C=O), a carbon-nitrogen double bond (C=N), a carbon-nitrogen triple bond (C≡N), or the like, in the presence of hydrogen.

The hydrogenation catalyst preferably contains a transition metal element, and specifically, preferably contains one or more selected from the group consisting of palladium, platinum, ruthenium, rhodium, rhenium, nickel, cobalt, iron, iridium, osmium, copper and chromium, more preferably contains one or more selected from the group consisting of palladium, platinum, ruthenium, rhodium, nickel, cobalt, iron, copper and chromium.

The hydrogenation catalyst may be a homogeneous hydrogenation catalyst or a heterogeneous hydrogenation catalyst. Any hydrogenation catalyst can be used in the present invention. The hydrogenation catalyst used in the present invention is preferably a heterogeneous hydrogenation catalyst since it is easy to separate the 5-cyanovaleramide hydrogenation reaction mixture to be described later from the hydrogenation catalyst and also it is easy to recover and reuse the hydrogenation catalyst after the reaction.

The homogeneous hydrogenation catalyst means a hydrogenation catalyst that dissolves in an aqueous solvent, and more specifically, means an organometallic complex having a hydrogenation ability. Examples of such a catalyst include Wilkinson's catalyst, Crabtree's catalyst, Shvo's catalyst, Schrock-Osborn catalyst, chiral phosphine-rhodium complex, phosphine-ethylenediamine-ruthenium complex, iridium PNP complex and the like.

The heterogeneous hydrogenation catalyst means a substance having a hydrogenating ability, which is insoluble in an aqueous solvent. Examples of such a catalyst include fine particle metal catalysts, sponge (porous) metal catalysts, supported organometallic complex catalysts, platinum oxide (Adams' catalyst), palladium oxide, palladium hydroxide (Pearlman's catalyst) and the like.

The fine particle metal catalyst is a fine-sized solid catalyst composed of a metal element. The particle size of the fine particle metal catalyst is not particularly limited, but may be any of sub-nano level, nano level, and micro level. From the viewpoints that, for example, the amount of metal used can be saved owing to an increase in the active surface, stability is improved through suppression of the aggregation of metal fine particles by supporting them, easiness of separation, and recovery and reuse of the catalyst is improved, in the case that the fine particle metal catalyst is used as the hydrogenation catalyst, it is preferable to use a supported metal catalyst having a structure where metal fine particles are supported on a carrier.

The supported metal catalyst can be prepared by a known method such as an impregnation method, a deposition-precipitation method, an ion exchange method, or a vapor-phase supporting method. Carriers that can be used in the preparation of the supported metal catalyst include carbon, polymers, metal oxides, metal sulfides, zeolites, clays, heteropolyacids, solid phosphoric acid, hydroxyapatite and the like.

The sponge (porous) metal catalyst is a porous metal catalyst obtained by eluting an amphoteric metal with an alkali from an alloy including a metal having hydrogenation catalytic activity and an amphoteric metal such as aluminum, zinc, or silicon. Specifically, a sponge cobalt catalyst, a sponge nickel catalyst, a sponge copper catalyst, a sponge iron catalyst or the like may be exemplified which are obtained by developing an alloy of a metal such as nickel, cobalt, copper or iron and aluminum with an alkali. These are also widely known as "Raney cobalt", "Raney nickel", "Raney copper", and "Raney iron" (all of which are registered trademarks of W. R. Grace & Co.).

The supported organometallic complex catalyst is a catalyst in which an organometallic complex is immobilized on a carrier via a linker ligand. As the carrier that can be used for preparing the supported organometallic complex catalyst, polymers, metal oxides and the like may be exemplified.

A co-catalyst may be added to the hydrogenation catalyst for the purpose of improving the catalytic activity of the hydrogenation catalyst and improving the stability, for example. As the co-catalyst, molybdenum, sulfur, bismuth and the like may be exemplified.

In the present invention, hydrogen refers to molecular hydrogen ($H_2$) unless otherwise specified.

Hydrogen to be reacted with 5-cyanovaleramide may be added to a reactor all at once or sequentially.

The partial pressure of hydrogen during the reaction is not particularly limited but, when it is too low, the reaction time will be lengthened. On the other hand, exceedingly high partial pressure of hydrogen is not desirable from the viewpoint of equipment safety. Therefore, the partial pressure at the start of the reaction is preferably atmospheric pressure or more and 10 MPa (gauge pressure) or less at room temperature, more preferably atmospheric pressure or more and 3 MPa (gauge pressure) or less at room temperature, and further preferably atmospheric pressure or more and 1 MPa (gauge pressure) or less at room temperature.

The mode of the reaction is not particularly limited, but the reaction can be carried out by any mode of batch tank reactor, a semi-batch tank reactor, a continuous tank reactor, a continuous tubular reactor and a trickle bed reactor. In the case where the reaction is carried out using a heterogeneous catalyst, the reaction can be carried out by any method of a suspension bed, a fixed bed, a moving bed and a fluidized bed.

The reaction temperature is not particularly limited, but when it is too low, the reaction rate will be slowed down, and when it is too high, the energy consumption will be increased and the final ε-caprolactam selectivity will become low, so that the cases are not preferable. From this point of view, the reaction temperature is preferably 25 to 250° C., more preferably 50 to 200° C., and even more preferably 80 to 150° C.

In addition to hydrogen, an inert gas such as nitrogen, helium or argon may coexist in the reactor.

On the other hand, since deterioration of the hydrogenation catalyst and generation of detonating gas are probable, the oxygen concentration in the reactor is preferably low and specifically, the concentration is preferably 5% by weight or less, more preferably 1% by weight or less, and even more preferably 0% by weight (i.e., in the absence of oxygen) with respect to the charged amount of 5-cyanovaleramide.

Further, from the viewpoint of reaction selectivity to ε-caprolactam, the amount of ammonia with respect to the aqueous solvent is preferably 3% by weight or less, more preferably 1% by weight or less, and even more preferably 0% by weight (i.e., in the absence of ammonia).

The amount of 5-cyanovaleramide charged to the aqueous solvent is not particularly limited, but a small amount thereof is industrially not preferable. From this point of view, the amount of 5-cyanovaleramide charged to the aqueous solvent is preferably 0.01% by weight or more, more preferably 0.1% by weight or more, and even more preferably 1.0% by weight or more.

The 5-cyanovaleramide hydrogenation reaction mixture, which is the product of the step (A), means a mixture of multiple products produced by reacting 5-cyanovaleramide with hydrogen in an aqueous solvent in the presence of a hydrogenation catalyst, as the embodiment described above. That is, the 5-cyanovaleramide hydrogenation reaction mixture refers to a substance which contains 6-aminocaproic acid amide as a main component, and in addition, contains a dimer of 6-aminocaproic acid amide, an oligomer. ε-caprolactam, unreacted 5-cyanovaleramide, and the like. Therefore, pure 6-aminocaproic acid amide is inconsistent with the 5-cyanovaleramide hydrogenation reaction mixture.

When the step (A) was performed in the presence of a homogeneous hydrogenation catalyst, the 5-cyanovaleramide hydrogenation reaction mixture produced in the aqueous solvent can be used in the step (B) without separating the catalyst and without taking out the mixture from the aqueous solvent.

In the case where the step (A) was performed with suspending the heterogeneous hydrogenation catalyst in an aqueous solvent, the 5-cyanovaleramide hydrogenation reaction mixture produced in the aqueous solvent may be used in the step (B) while the catalyst was suspended without taking out the mixture from the aqueous solvent. After separating the catalyst by a simple solid-liquid separation operation (filtration, centrifugation, decantation, etc.), the 5-cyanovaleramide hydrogenation reaction mixture may be used in the step (B) without being taken from the aqueous solvent.

The 5-cyanovaleramide hydrogenation reaction mixture produced in the aqueous solvent in the step (A) may be taken out from the aqueous solvent and further the 5-cyanovaleramide hydrogenation reaction mixture taken out from the aqueous solvent may be roughly or finely purified before the step (B). The rough or fine purification of the 5-cyanovaleramide hydrogenation reaction mixture can be performed by an ordinary separation operation such as filtration, extraction, distillation or crystallization.

In the case where unreacted 5-cyanovaleramide remains in the step (A), the yield of ε-caprolactam can be further improved by separating the unreacted 5-cyanovaleramide through the above-mentioned separation operation and by using it in the step (A) again.

The ratio of 6-aminocaproic acid amide contained in the 5-cyanovaleramide hydrogenation reaction mixture obtained in the step (A) is, from the viewpoint of obtaining ε-caprolactam in high yield in the subsequent step (B), preferably 45 mol % or more and 72 mol % or less, more preferably 50 mol % or more and 71 mol % or less, and further preferably 60 mol % or more and 70 mol % or less. The ratio of 6-aminocaproic acid amide here is the molar ratio of 6-aminocaproic acid amide to the substance (including unreacted 5-cyanovaleramide) contained in the 5-cyanovaleramide hydrogenation reaction mixture. Since all the substances contained in the 5-cyanovaleramide hydrogenation reaction mixture can be regarded to be derived from the 5-cyanovaleramide before the hydrogenation reaction, the molar ratio of 6-aminocaproic acid amide to the 5-cyanovaleramide charged in the step (A) can be regarded as the ratio of 6-aminocaproic acid amino contained in the 5-cyanovaleramide hydrogenation reaction mixture.

[Step (B)]

In the step (B), the 5-cyanovaleramide hydrogenation reaction mixture obtained in the step (A) is heated at a temperature of 180 to 300° C. in an aqueous solvent to obtain ε-caprolactam.

In the step (B). ε-caprolactam can be obtained in high yield by heating the 5-cyanovaleramide hydrogenation reaction mixture in an aqueous solvent at a temperature of 180 to 300° C. The temperature range is more preferably 200 to 280° C., further preferably 220 to 260° C. The above-mentioned solvent is used as the aqueous solvent, but the aqueous solvent used in the step (A) and the aqueous solvent used in the step (B) are not necessarily the same solvent.

The mode of the reaction is not particularly limited, but the reaction can be carried out by any mode of a batch tank reactor, a semi-batch tank reactor, a continuous tank reactor, a continuous tubular reactor and a trickle bed reactor. In the case where the reaction is carried out using a heterogeneous catalyst, the reaction can be carried out by any method of a suspension bed, a fixed bed, a moving bed and a fluidized bed.

An inert gas such as nitrogen, helium or argon may be present in the reactor.

In order to suppress the sequential oxygenation of ε-caprolactam, the oxygen concentration in the reactor is preferably low. Specifically, the concentration is preferably 5% by weight or less, more preferably 1% by weight or less, and even more preferably 0% by weight (i.e., in the absence of oxygen) with respect to the charged amount of 5-cyanovaleramide.

In order to suppress the sequential hydrogenation of ε-caprolactam, the hydrogen concentration in the reactor is preferably low. Specifically, the concentration is preferably 5% by weight or less, more preferably 1% by weight or less, and even more preferably 0% by weight (i.e., in the absence of hydrogen) with respect to the charged amount of 5-cyanovaleramide. Therefore, in the case where the step (B) is continuously performed from the step (A), the hydrogen existing in the step (A) is preferably purged to the outside of the reaction system before the step (B).

Further, from the viewpoint of reaction selectivity to ε-caprolactam, the amount of ammonia with respect to the aqueous solvent is preferably 3% by weight or less, more preferably 1% by weight or less, and even more preferably 0% by weight (i.e., in the absence of ammonia).

Step (B) can be usually performed in the absence of a catalyst, but may be performed in the presence of a catalyst. When a catalyst is used, an acid catalyst is preferably used, and particularly, a heterogeneous acid catalyst is more preferably used. Specifically, as the heterogeneous acid catalyst, polymers, metal oxides, metal sulfides, zeolites, clays, heteropolyacids, solid phosphoric acid, hydroxyapatite and the like may be given as examples.

As the polymer having acid catalytic activity, acid ion exchange resins may be given as an example. Specifically, a styrene-based sulfonic acid-type ion exchange resin and a phenol-based sulfonic acid-type ion exchange resin can be used.

Examples of the metal oxide having acid catalytic activity include oxides containing one or more metal elements selected from the group consisting of Sc, Y, Ce, Ti, Zr, V, Nb, Ta, Cr, Mo, W, Mn, Fe, Zn, Cd, Al, Ga, In, Si, Ge, Sn, and Pb. More specifically, scandium oxide ($Sc_2O_3$), cerium oxide ($CeO_2$), anatase-type titanium oxide (A-$TiO_2$), rutile-type titanium oxide (R—$TiO_2$), zirconium oxide ($ZrO_2$), vanadium oxide ($V_2O_5$), niobium oxide ($Nb_2O_5$), tantalum oxide ($Ta_2O_5$), chromium oxide ($Cr_2O_3$), molybdenum oxide ($MoO_3$), tungsten oxide ($WO_3$), manganese oxide ($MnO_2$), iron oxide ($Fe_2O_3$, $Fe_3O_4$), zinc oxide (ZnO), aluminum oxide ($Al_2O_3$), gallium oxide ($Ga_2O_3$), indium oxide ($In_2O_3$), silicon dioxide ($SiO_2$), germanium oxide ($GeO_2$), tin oxide ($SnO_2$), lead oxide (PbO), silica-alumina ($SiO_2$—$Al_2O_3$), and the like can be given as examples. As these metal oxides, porous ones having a large specific surface area may be used. For example, mesoporous silica, mesoporous titania and the like can be preferably used.

As examples of the zeolite having acid catalytic activity, a zeolite having a structural code consisting of a three-letter alphabet in the database of International Zeolite Association can be given. More specifically, zeolites having structural codes such as LTA, FER, MWW, MFI, MOR, LTL, FAU, BEA, CHA, and CON can be given as examples.

Examples of the clay having acid catalytic activity include kaolin, montmorillonite, bentonite, saponite, and acidic clay.

The ε-caprolactam obtained in the step (B) is an ε-caprolactam composition containing a small amount of 6-aminocaproic acid amide in addition to ε-caprolactam. In the ε-caprolactam composition, the ratio of 6-aminocaproic acid amide to ε-caprolactam is, from the viewpoint of process efficiency, preferably 0.1 mol % or more and 5 mol % or less, more preferably 0.2 mol % or more and 4 mol % or less, and even more preferably 0.5 mol % or more and 3 mol % or less. When the ratio is less than 0.1 mol %, the progress of the polyamide polymerization in the subsequent stage is slowed down, while when it exceeds 5 mol %, the load in the recovery step tends to increase.

[Recovery of ε-Caprolactam]

The ε-caprolactam produced by the method of producing ε-caprolactam of the present invention can be recovered by ordinary separation and purification operations such as filtration, extraction, distillation and crystallization after the reaction.

[Polyamide Polymerization]

The ε-caprolactam obtained by the method of producing ε-caprolactam of the present invention can be used as a raw material for producing a polyamide. As a method of producing a polyamide, a known method for ring-opening polymerization of ε-caprolactam can be applied (see Osamu Fukumoto. "Polyamide Resin Handbook", THE NIKKAN KOGYO SHIMBUN, LTD. (January 1998)).

EXAMPLES

Hereinafter, the present invention will be described in more detail with reference to Examples, but the present invention is not limited to the following Examples. The reaction yield is defined by the following formula.

Product yield (mol %)=Amount (mol) of product produced/Amount (mol) of 5-cyanovaleramide charged×100.

Ratio (mol %) of 6-aminocaproic acid amide in 5-cyanovaleramide hydrogenation reaction mixture (Product of step (A))=Amount (mol) of 6-aminocaproic acid amide produced after step (A)/Amount (mol) of 5-cyanovaleramide charged×100.

Ratio (mol %) of 6-aminocaproic acid amide to ε-caprolactam=Amount (mol) of 6-aminocaproic acid amide produced after step (B)/Amount (mol) of ε-caprolactam produced after step (B)×100.

Each reaction solution was analyzed by high performance liquid chromatography (HPLC). The qualification and quantification of the product was performed by an absolute calibration curve prepared using specimen. The analytical conditions for HPLC are shown below.

[Analytical Conditions of HPLC]

HPLC apparatus: Prominence (manufactured by Shimadzu Corporation)

Column: Synergi hydro-RP (manufactured by Phenomenex), length 250 mm, inner diameter 4.60 mm, particle size 4 μm Mobile phase: 0.1 wt % phosphoric acid aqueous solution/acetonitrile=95/5 (volume ratio)

Flow rate: 1.0 mL/min

Detector: UV (210 nm)

Column temperature: 40° C.

Example 1

[Step (A)]

Into a stainless steel autoclave (manufactured by Taiatsu Garasu Kogyo K.K.) having an internal volume of 0.2 L were added 0.1 g of 5-cyanovaleramide (manufactured by Enamine Ltd.), 100 mL of water, 0.035 g of powdered sponge cobalt catalyst R-401 (manufactured by Nikko Rica Corporation). After purging the inside of the autoclave with nitrogen while stirring at a stirring rate of 1000 rpm, hydrogen gas was introduced so that the partial pressure of hydrogen in the autoclave became 3.5 MPa (gauge pressure). Then, the temperature in the autoclave was raised to 100° C. After holding at 100° C. for 5 hours, the mixture was allowed to cool to room temperature, the gas in the autoclave was released to return the pressure to normal pressure, and then the reaction solution was recovered. The supernatant from which the catalyst had been removed by filtration was analyzed by HPLC. Table 1-1 shows the results.

[Step (B)]

The aqueous solution containing the 5-cyanovaleramide hydrogenation reaction mixture obtained in the step (A) was added again to a stainless steel autoclave (manufactured by Taiatsu Garasu Kogyo K.K.) having an internal volume of 0.2 L. After purging the inside of the autoclave with nitrogen, nitrogen gas was introduced so that the partial pressure of nitrogen in the autoclave became 0.5 MPa (gauge pressure). Then, the temperature in the autoclave was raised to 250° C. After holding at 250° C. for 1 hour, the mixture was allowed to cool to room temperature, the gas in the autoclave was released to return the pressure to normal pressure, and then the reaction solution was recovered and analyzed by HPLC. Table 1-1 shows the results.

Example 2

The reaction was carried out in the same manner as in Example 1 except that the hydrogen partial pressure in the step (A) was held at 1.0 MPa (gauge pressure) at 100° C. for 3 hours. Table 1-1 shows the results.

Example 3

The reaction was carried out in the same manner as in Example 2 except that "Raney nickel" (manufactured by FUJIFILM Wako Pure Chemical Corporation) was used as the catalyst. Table 1-1 shows the results.

Comparative Example 1

The reaction was carried out in the same manner as in Example 1 except that t-butanol (manufactured by FUJIFILM Wako Pure Chemical Corporation) was used as the solvent. Table 1-1 shows the results.

Comparative Example 2

The reaction was carried out in the same manner as in Example 1 except that methanol (manufactured by FUJIFILM Wako Pure Chemical Corporation) was used as the solvent. Table 1-1 shows the results.

Comparative Example 3

The reaction was carried out in the same manner as in Example 1 except that dioxane (manufactured by FUJIFILM Wako Pure Chemical Corporation) was used as the solvent. Table 1-1 shows the results.

Example 4

The reaction was carried out in the same manner as in Example 1 except that the reaction time in the step (A) was set to 1 hour. Table 1-2 shows the results.

Example 5

The reaction was carried out in the same manner as in Example 1 except that the reaction temperature in the step (A) was set to 120° C. and the reaction temperature in the step (B) was set to 260° C. Table 1-2 shows the results.

Example 6

[Step (A)]

Into a stainless steel autoclave (manufactured by Taiatsu Garasu Kogyo K.K.) having an internal volume of 0.1 L were added 0.1 g of 5-cyanovaleramide (manufactured by Enamine Ltd.), 30 mL of water, and 0.033 g of ruthenium-supported aluminum oxide (manufactured by N. E. Chemcat Corporation). After purging the inside of the autoclave with nitrogen while stirring at a stirring rate of 500 rpm, hydrogen gas was introduced so that the partial pressure of hydrogen in the autoclave became 0.9 MPa (gauge pressure). Then, the temperature in the autoclave was raised to 80° C. After holding at 80° C. for 5 hours, the mixture was allowed to cool to room temperature and the gas in the autoclave was released to return the pressure to normal pressure. The supernatant from which the catalyst had been removed by filtration was analyzed by HPLC. Table 1-2 shows the results.

[Step (B)]

The aqueous solution containing the 5-cyanovaleramide hydrogenation reaction mixture obtained in the step (A) was added again to a stainless steel autoclave (manufactured by Taiatsu Garasu Kogyo K.K.) having an internal volume of 0.1 L. After purging the inside of the autoclave with nitrogen, nitrogen gas was introduced so that the partial pressure of nitrogen in the autoclave became 0.5 MPa (gauge pressure). Then, the temperature in the autoclave was raised to 240° C. After holding at 240° C. for 1 hour, the mixture was allowed to cool to room temperature, the gas in the autoclave was released to return the pressure to normal pressure, and then the reaction solution was recovered and analyzed by HPLC. Table 1-2 shows the results.

Example 7

The reaction was carried out in the same manner as in Example 6 except that the catalyst of the step (A) was changed to nickel-supported silicon dioxide-aluminum oxide (manufactured by Alfa Aesar), the reaction temperature was set to 100° C., and the reaction temperature of the step (B) was set to 250° C. Table 1-2 shows the results.

Example 8

The reaction was carried out in the same manner as in Example 6 except that a water/methanol mixed solvent (90% by volume of water) was used as the solvent instead of water and the reaction temperature at the step (B) was set to 250° C. Table 1-2 shows the results.

Example 9

The reaction was carried out in the same manner as in Example 8 except that a water/methanol mixed solvent (60% by volume of water) was used as the solvent. Table 1-2 shows the results.

Example 10

The reaction was carried out in the same manner as in Example 8 except that a water/dioxane mixed solvent (90% by volume of water) was used as the solvent. Table 1-2 shows the results.

Example 11

The reaction was carried out in the same manner as in Example 8 except that a water/t-butanol mixed solvent (90% by volume of water) was used as the solvent. Table 1-2 shows the results.

Comparative Example 4

The reaction was carried out in the same manner as in Example 1 except that a water/t-butanol mixed solvent (10% by volume of water) was used as the solvent. Table 1-2 shows the results.

the presence of a hydrogenation catalyst (step (A)), and ε-caprolactam can be synthesized in high yield by the step of heating the 5-cyanovaleramide hydrogenation reaction mixture obtained in the step A at 180 to 300° C. in an aqueous solvent (step (B)). Further, the comparison between Examples 1 to 3 and Comparative Examples 1 to 3 showed

TABLE 1-1

| | | | | Results of step (A) | | | Results of steps (A) + (B) | | |
|---|---|---|---|---|---|---|---|---|---|
| | Solvent | Conditions of step (A) | Conditions of step (B) | Yield of ACAm (mol %) | Yield of ε-CL (mol %) | Ratio of ACAm in product of step (A) (mol %) | Yield of ACAm (mol %) | Yield of ε-CL (mol %) | Ratio of ACAm to ε-CL (mol %) |
| Example 1 | water | $H_2$ 3.5 MPa (G) sponge Co 100° C., 5 h | $N_2$ 0.5 MPa (G) no catalyst 250° C., 1 h | 68.1 | 12.5 | 68.1 | 1.4 | 89.7 | 1.6 |
| Example 2 | water | $H_2$ 1.0 MPa (G) sponge Co 100° C., 3 h | $N_2$ 0.5 MPa (G) no catalyst 250° C., 1 h | 70.2 | 0.4 | 70.2 | 2.2 | 84.7 | 2.6 |
| Example 3 | water | $H_2$ 1.0 MPa (G) Raney Ni 100° C., 3 h | $N_2$ 0.5 MPa (G) no catalyst 250° C., 1 h | 67.7 | 0.5 | 67.7 | 1.8 | 86.5 | 2.1 |
| Comparative Example 1 | t-butanol | the same as in Example 1 | | 3.7 | 1.1 | 3.7 | 0.9 | 2.5 | 36 |
| Comparative Example 2 | methanol | the same as in Example 1 | | 56.9 | 0.9 | 56.9 | 18.0 | 19.5 | 92 |
| Comparative Example 3 | dioxane | the same as in Example 1 | | 8.0 | 0.4 | 8.0 | 5.1 | 1.8 | 283 |

ACAm: 6-aminocaproic acid amide,
ε-CL: ε-caprolactam

TABLE 1-2

| | | | | Results of step (A) | | | Results of steps (A) + (B) | | |
|---|---|---|---|---|---|---|---|---|---|
| | Solvent | Conditions of step (A) | Conditions of step (B) | Yield of ACAm (mol %) | Yield of ε-CL (mol %) | Ratio of ACAm in product of step (A) (mol %) | Yield of ACAm (mol %) | Yield of ε-CL (mol %) | Ratio of ACAm to ε-CL (mol %) |
| Example 4 | water | $H_2$ 3.5 MPa (G) sponge Co 100° C., 1 h | $N_2$ 0.5 MPa (G) no catalyst 250° C., 1 h | 53.4 | 0.3 | 53.4 | 0.9 | 82.1 | 1.1 |
| Example 5 | water | $H_2$ 3.5 MPa (G) sponge Co 120° C., 5 h | $N_2$ 0.5 MPa (G) no catalyst 260° C., 1 h | 61.2 | 4.4 | 61.2 | 0.4 | 87.5 | 0.5 |
| Example 6 | water | $H_2$ 0.9 MPa (G) Ru/$Al_2O_3$ 80° C., 5 h | $N_2$ 0.5 MPa (G) no catalyst 240° C., 1 h | 64.3 | undetected | 64.3 | 2.7 | 81.1 | 3.3 |
| Example 7 | water | $H_2$ 0.9 MPa (G) Ni/$SiO_2$ 100° C., 5 h | $N_2$ 0.5 MPa (G) no catalyst 250° C., 1 h | 58.5 | 0.6 | 58.5 | 1.1 | 88.3 | 1.2 |
| Example 8 | water/methanol 9/1 v/v | $H_2$ 0.9 MPa (G) Ru/$Al_2O_3$ 80° C., 5 h | $N_2$ 0.5 MPa (G) no catalyst 250° C., 1 h | 66.3 | 7.3 | 66.3 | 0.9 | 87.4 | 1.0 |
| Example 9 | water/methanol 6/4 v/v | the same as in Example 8 | | 70.6 | 7.8 | 70.6 | 0.3 | 84.3 | 0.4 |
| Example 10 | water/dioxane 9/1 v/v | the same as in Example 8 | | 63.2 | 7.1 | 63.2 | 1.5 | 86.4 | 1.7 |
| Example 11 | water/t-butanol 9/1 v/v | the same as in Example 8 | | 71.4 | 3.4 | 71.4 | 1.1 | 89.4 | 1.2 |
| Comparative Example 4 | water/t-butanol 1/9 v/v | the same as in Example 1 | | 2.2 | undetected | 2.2 | 0.2 | 1.1 | 18 |

ACAm: 6-aminocaproic acid amide,
ε-CL: ε-caprolactam

Examples 1 to 3 showed that a 5-cyanovaleramide hydrogenation reaction mixture containing 6-aminocaproic acid amide as a main product is obtained by the step of reacting 5-cyanovaleramide with hydrogen in an aqueous solvent in that it is important to use an aqueous solvent in the steps (A) and (B) in order to synthesize ε-caprolactam in high yield.

Examples 4 to 7 showed that the steps (A) and (B) can be performed with various reaction temperatures, reaction times and catalysts. Examples 8 to 11 and Comparative Example 4 showed that it is preferable to use a water-containing water-miscible organic solvent containing more than 10% by volume of water as a solvent.

The invention claimed is:

1. A method of producing ε-caprolactam, the method comprising the following steps (A) and (B):
   (A) a step of reacting 5-cyanovaleramide with hydrogen in an aqueous solvent in a presence of a hydrogenation catalyst to obtain a 5-cyanovaleramide hydrogenation reaction mixture;
   (B) a step of heating the 5-cyanovaleramide hydrogenation reaction mixture at a temperature of 180° C. or higher and 300° C. or lower in an aqueous solvent to obtain ε-caprolactam.

2. The method according to claim 1, wherein the step (A) is performed in an absence of ammonia.

3. The method according to claim 1, wherein a reaction temperature in the step (A) is 50° C. or higher and 200° C. or lower.

4. The method according to claim 1, wherein the temperature of the step (B) is 200° C. or higher and lower than 280° C.

5. The method according to claim 1, wherein the step (B) is performed in an absence of a catalyst.

6. The method according to claim 1, wherein a ratio of 6-aminocaproic acid amide contained in the 5-cyanovaleramide hydrogenation reaction mixture is 45 mol % or more and 72 mol % or less.

7. An ε-caprolactam composition having a ratio of 6-aminocaproic acid amide to ε-caprolactam of 0.1 mol % or more and 5 mol % or less, and comprising no ammonia.

* * * * *